United States Patent [19]
Modney

[11] Patent Number: 6,014,432
[45] Date of Patent: Jan. 11, 2000

[54] HOME HEALTH CARE SYSTEM

[75] Inventor: David L. Modney, Fairport, N.Y.

[73] Assignee: Eastman Kodak Company, Rochester, N.Y.

[21] Appl. No.: 09/081,318

[22] Filed: May 19, 1998

[51] Int. Cl.[7] .............................. H04M 11/00; H04N 7/14; A61B 7/04

[52] U.S. Cl. .......................... 379/106.02; 348/17; 381/67; 600/300

[58] Field of Search .............................. 379/37–38, 93.31, 379/93.33, 93.37, 106.01–106.02, 101.01, 93.08, 102.01–102.02; 348/14–17, 390; 600/300, 509, 513; 128/903–904; 381/67, 320, 106; 704/219–220, 500; 707/10; 375/356

[56] References Cited

U.S. PATENT DOCUMENTS

| | | | |
|---|---|---|---|
| 3,742,938 | 7/1973 | Stern | 600/500 |
| 3,810,102 | 5/1974 | Parks, III et al. | 703/5 |
| 3,898,373 | 8/1975 | Walsh | 375/356 |
| 4,097,691 | 6/1978 | Ehrlich et al. | 379/444 |
| 4,337,377 | 6/1982 | VanRiper et al. | 379/106.02 |
| 4,428,381 | 1/1984 | Hepp | 600/528 |
| 4,622,979 | 11/1986 | Katchis et al. | 128/904 |
| 4,883,064 | 11/1989 | Olson et al. | 600/509 |
| 5,321,618 | 6/1994 | Gessman | 379/106.02 |
| 5,339,821 | 8/1994 | Fujimoto | 600/513 |
| 5,357,427 | 10/1994 | Langen et al. | 600/300 |
| 5,467,773 | 11/1995 | Bergelson et al. | 600/522 |
| 5,474,090 | 12/1995 | Begun et al. | 600/520 |
| 5,522,396 | 6/1996 | Langer et al. | 600/509 |
| 5,539,452 | 7/1996 | Bush et al. | 348/17 |
| 5,544,649 | 8/1996 | David et al. | 348/14 |
| 5,546,395 | 8/1996 | Sharma et al. | 704/219 |
| 5,550,902 | 8/1996 | Abbruscato | 379/106.02 |
| 5,594,786 | 1/1997 | Chaco et al. | 379/106.02 |
| 5,611,038 | 3/1997 | Shaw et al. | 348/390 |
| 5,666,404 | 9/1997 | Ciccotelli et al. | 379/106.02 |
| 5,704,364 | 1/1998 | Saltzstein et al. | 600/300 |
| 5,709,216 | 1/1998 | Woodson, III | 600/300 |
| 5,867,821 | 2/1999 | Ballantyne et al. | 707/10 |

OTHER PUBLICATIONS

J.L. Crouch et al, Electrocardiograms By Telephone, Bell Laboratories Record, Feb. 1966.

*Primary Examiner*—Curtis A. Kuntz
*Assistant Examiner*—George Eng
*Attorney, Agent, or Firm*—William F. Noval

[57] ABSTRACT

A home health care system comprising: patient station including a first videophone, an electronic imaging assembly and a stethoscope assembly, coupled to said first videophone, for respectively producing digital image and physiological sound signals of a patient, wherein said first videophone simultaneously transmits said digital signals over a public telecommunications network; and a health care provider's station including a second videophone, a video display and a sound reproducer, wherein the second videophone receives digital signals from the first videophone over the public telecommunications network, displays the images of the patient on the display, and reproduces the physiological sounds of the patient by the sound reproducer.

1 Claim, 3 Drawing Sheets

HOME HEALTH CARE SYSTEM

FIELD OF THE INVENTION

This invention relates in general to home health care systems and relates more particularly to a home health care system in which video images and physiological data of a patient are digitally transmitted from a patient's video phone to a remote video phone of a health care provider over a public telecommunication network (telephone system).

BACKGROUND OF THE INVENTION

There exists a need for a home health care system in which both images and physiological data of a patient at home can be examined by a health care provider (doctor, nurse) at a remote location. The relentless pressure to reduce costs in the health care industry requires more efficient use of a health care professional's services. Although office visits are typical, many patients are either too ill, disabled, or too remote from a health care professional's office to be able to avail oneself of an office visit. As a result, home health care systems have been proposed that allow transmission of physiological data of a patient at home to a health care professional at a remote locate over a public telecommunication network, such as the public telephone system. The following patents and publication disclose various home health care systems using the common telephone to transmit physiological data of a patient, such as body sounds produced by a stethoscope, electrocardiogram (EKG) signals, blood pressure, artificial heart valve clicks, etc.

U.S. Pat. No. 5,550,902, issued Aug. 27, 1996, inventor Abbruscato.

U.S. Pat. No. 5,339,821, issued Aug. 23, 1994, inventor Fujimoto.

U.S. Pat. No. 4,883,064, issued Nov. 28, 1989, inventors Olson et al.

U.S. Pat. No. 4,097,691, issued Jun. 27, 1978, inventors Ehrlich et al.

U.S. Pat. No. 3,742,938, issued Jul. 3, 1973, inventor Stern.

U.S. Pat. No. 4,622,979, issued Nov. 18, 1986, inventors Katchis et al.

U.S. Pat. No. 4,428,381, issued Jan. 31, 1984, inventor Hepp.

U.S. Pat. No. 3,810,102, issued May 7, 1974, inventors Parks III, et al.

U.S. Pat. No. 5,666,404, issued Sep. 9, 1997, inventors Ciccotelli et al.

U.S. Pat. No. 5,474,090, issued Dec. 12, 1995, inventors Begun et al.

U.S. Pat. No. 5,321,618, issued Jun. 14, 1994, inventor Gessman.

U.S. Pat. No. 5,357,427, issued Oct. 18, 1994, inventor Langen et al.

U.S. Pat. No. 5,467,773, issued Nov. 21, 1995, inventors Bergelson et al.

U.S. Pat. No. 5,522,396, issued Jun. 4, 1996, inventors Langer et al.

U.S. Pat. No. 5,704,364, issued Jan. 6, 1998, inventors Saltzstein et al.

U.S. Pat. No. 4,337,377, issued Jun. 29, 1982, inventors Van Riper et al.

J. L. Crouch et al, *Electrocardiograms By Telephone*, Bell Laboratories Record, February 1966.

These systems are disadvantageous for one or more of the following reasons.

1. The physiological data is transmitted as analog signals which are susceptible to noise and signal degradation resulting in corruption of the transmitted data.

2. Visual images of the patient are not transmitted.

3. The system is expensive, inconvenient, and/or inefficient.

SUMMARY OF THE INVENTION

According to the present invention, there is provided a solution to these problems.

According to a feature of the present invention, there is provided a home health care system comprising: patient station including a first videophone, an electronic imaging assembly and a stethoscope assembly, coupled to said first videophone, for respectively producing digital image and physiological sound signals of a patient, wherein said first videophone simultaneously transmits said digital signals over a public telecommunications network; and a health care provider's station including a second videophone, a video display and a sound reproducer, wherein the second videophone receives digital signals from the first videophone over the public telecommunications network, displays the images of the patient on the display, and reproduces the physiological sounds of the patient by the sound reproducer.

ADVANTAGEOUS EFFECT OF THE INVENTION

The invention has the following advantages.

1. Physiological data of a patient are transmitted digitally over a public telecommunication network, minimizing degradation and corruption of the data. The health care provider can thus provide a more reliable diagnosis of the patient.

2. Visual images of the patient are digitally transmitted simultaneously with the physiological data, thus enhancing communication between patient and health care provider, and optimizing proper diagnosis.

3. The home health care system is cost effective, uses public telecommunication networks, such as the public telephone network, and is convenient to both patient and health care provider.

4. The patient's physiological sounds are stored at the patient station at full resolution, but are initially transmitted to the health care provider's station in a compressed format. Because the data compressor is selectively controllable to compress data at different compression ratios, the health care provider can command the patient station to retransmit the physiological data at a lower compression ratio, thus producing higher quality sound.

DETAILED DESCRIPTION OF THE INVENTION

Figure 1:
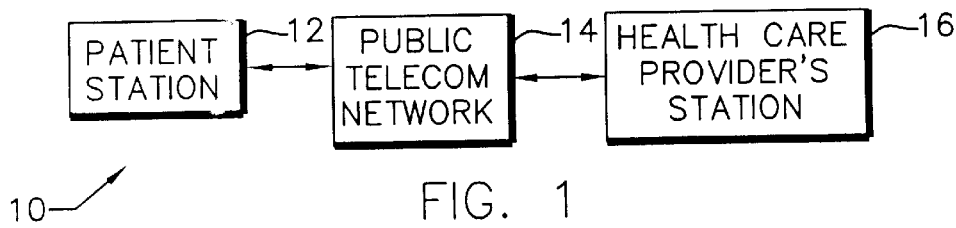
FIG. 1 is a block diagram of a home health care system according to the present invention.

Referring now to the figures, there is shown a preferred embodiment of the present invention. FIG. 1 is a block diagram of the main components of a home health care system of the invention. As shown, home health care system 10 includes a patient station 12, a health care provider's station 16, and a public telecommunication network 14 connecting stations 12 and 16. Network 14 can, for example, be the public telephone network, cellular phone network, ISDN, Ethernet, Intranet, Internet, or any other network capable of transmitting digital signals between stations 12 and 16.

In general, each of stations 12 and 16, is provided with a videophone which is connected to network 14. The patient station is located at a patient's venue, such as, the patient's home. The health care provider's station is located at the provider's venue, such as a doctor's or nurse's office, a hospital, or the like. As will be described in more detail later, the patient's station includes a stethoscope which is used by the patient to produce physiological sounds of the patient. The physiological sounds relate to the cardiovascular and respiratory systems of the patient. The sounds are digitized and transmitted by station 12 over network 14 to station 16, where they are reproduced and examined by the health care provider. Images of the patient are simultaneously transmitted over network 14 to enhance the examination and diagnosis of the patient.

Figure 2:
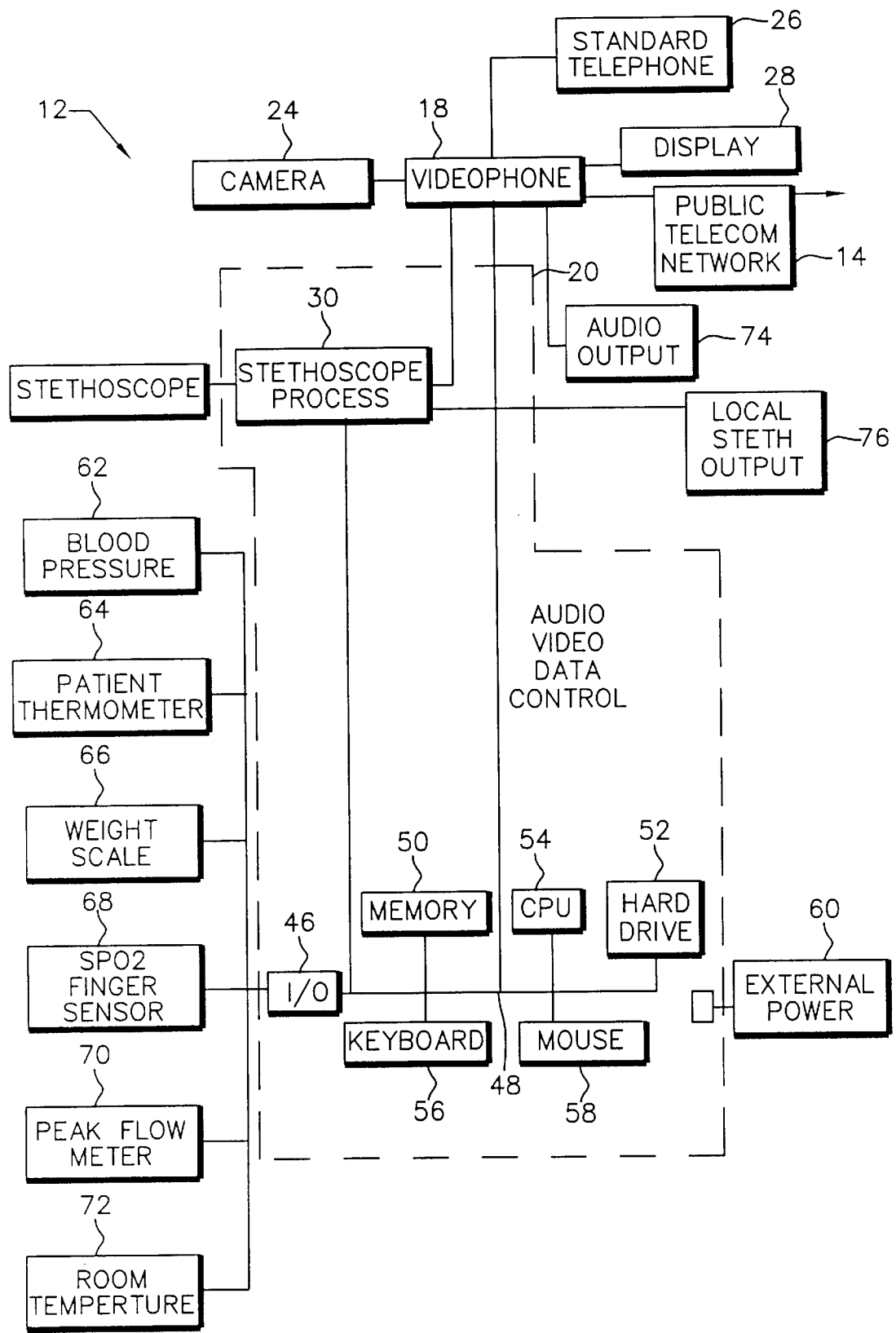
FIG. 2 is a block diagram of a patient's station of the system of FIG. 1.

Referring now to FIG. 2, there will be described a preferred embodiment of patient station 12. As shown, station 12 includes a first videophone 18, a processor 20, and a stethoscope 22. Videophone 18 is a standard videophone (e.g., an 8×8 VC50/55) which sends and receives audio and video as digital data over a standard public telephone network 14, or the like. Coupled to videophone 18 are camera 24 for capturing images of a patient, a standard telephone 26, and a video display 28 for displaying images, graphics and data. Processor 20 includes a stethoscope processing circuit 30 for converting patient physiological sounds picked up by stethoscope 22 into compressed digital data transmitted by videophone 18 over network 14 to station 16.

Figure 3:
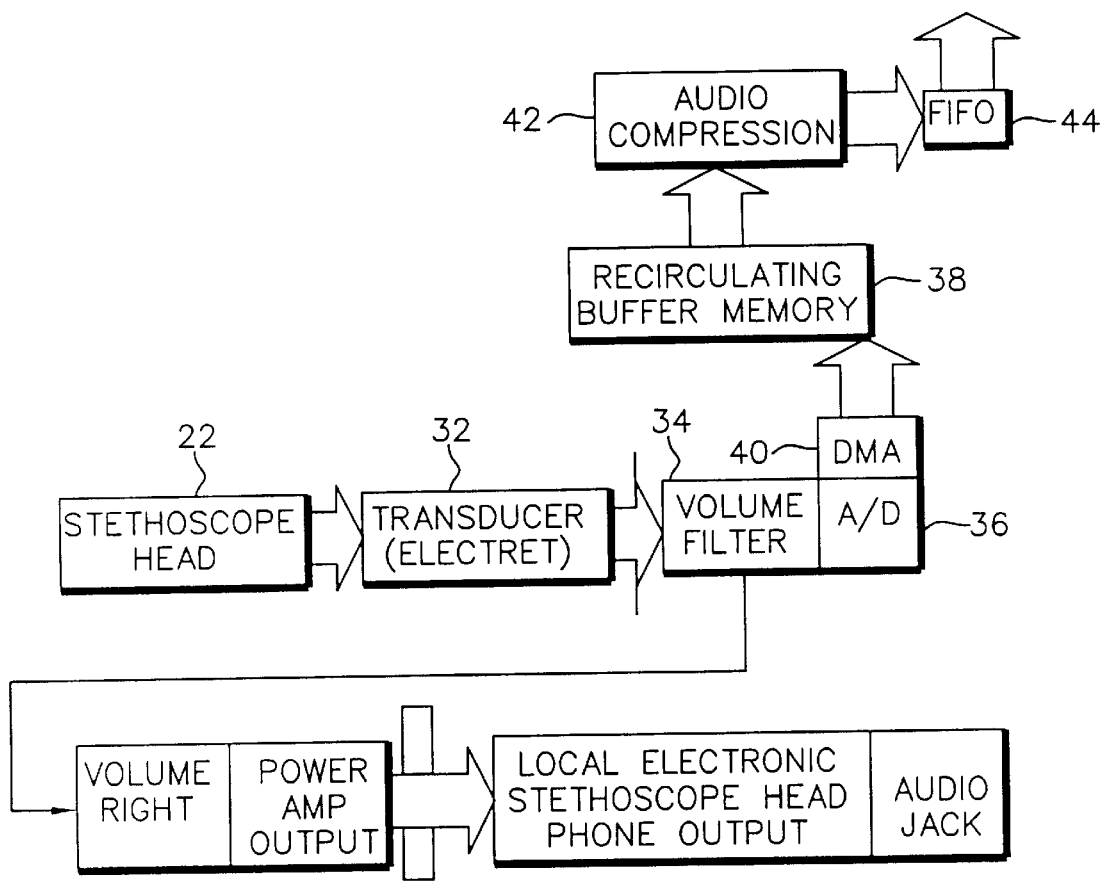
FIG. 3 is a block diagram of a preferred stethoscope sound processing circuit.

As shown in greater detail in FIG. 3, stethoscope processing circuit 30 includes a transducer 32 for converting the physiological sounds into analog signals, a volume and filter section 34, an analog to digital converter 36 for converting the analog signals to digital data, and a recirculating buffer memory 38 controlled by direct memory access controller (DMA) 40. Buffer memory 38 stores many seconds of the raw high quality digital physiological sounds data. The digital data is compressed by a tunable loss audio compressor 42. If the health care provider at station 16 wishes to listen to high quality audio at a later time, the recirculating buffer memory 38 can be accessed to recompress the digital data at a different loss level (compression ratio) to produce higher quality audio. The new data is retransmitted. The compressed digital data is stored in a first-in-first-out (FIFO) memory 44. The data from memory 44 is sent to a data channel of videophone 18. The data is then transmitted over network 14 to station 16 along with digital images of the patient.

Referring again to FIG. 2, processor 20 also includes an input/output (I/O) 46, bus 48, memory 50, hard drive 52 for storing an operating system, programs, and data, CPU 54, keyboard 56, and mouse 58. Processor 20 can be powered by an internal battery or an external power source 60. Other devices can be connected to processor 20 for transmission of other patient physiological data. These devices include blood pressure device 62, patient thermometer 64, weight scale 66, SpO2 finger sensor 68, peak flow meter 70, and room temperature device 72. The values produced by these devices are digitized by processor 20 and sent by videophone 18 over network 14 in a videophone data channel. Station 12 also includes audio output (speaker) 74 and local stethoscope output 76 (headphones).

Figure 4:
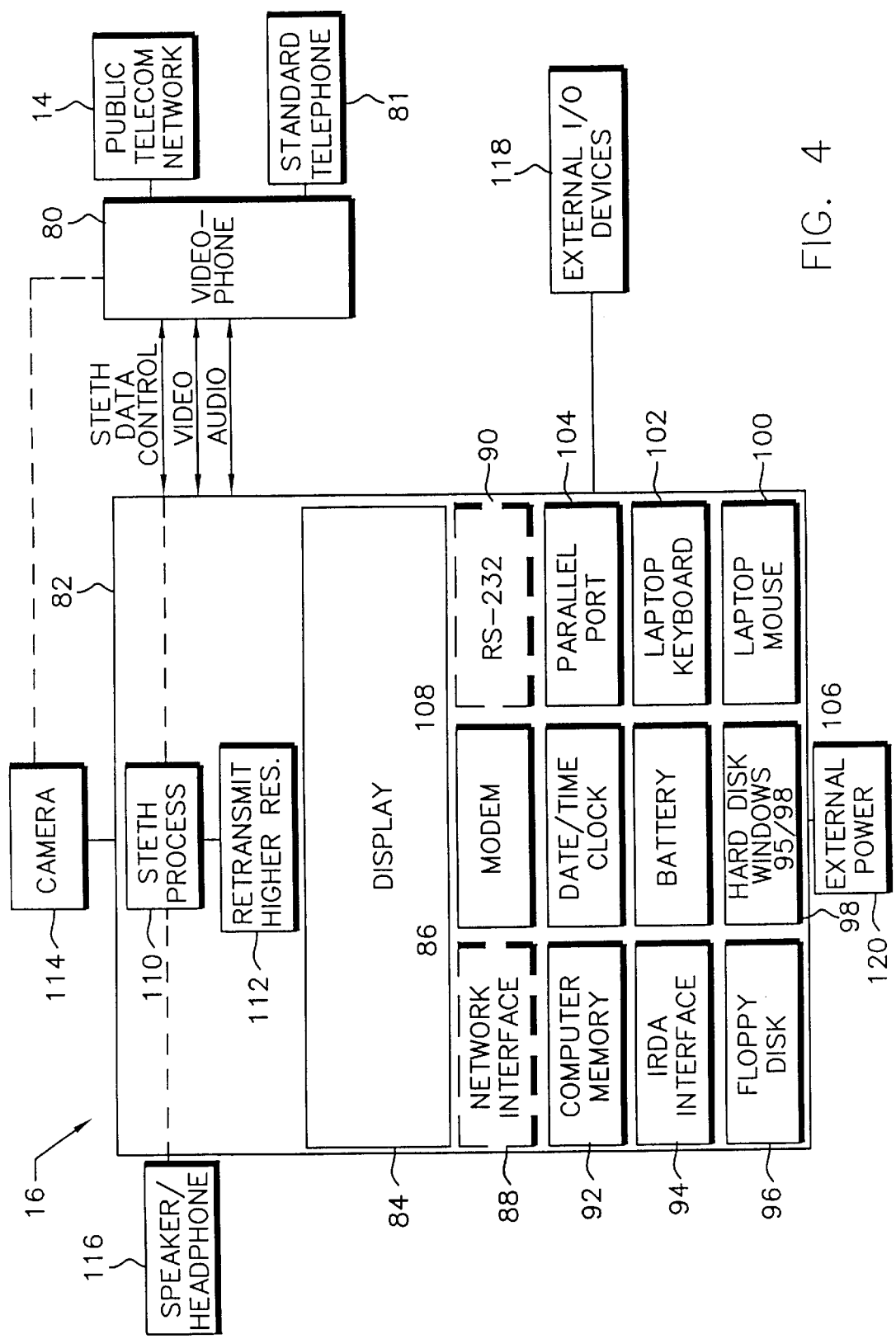
FIG. 4 is a block diagram of a health care provider's station of the system of FIG. 1.

Referring now to FIG. 4, there is shown in greater detail station 16. As shown, station 16 includes a second videophone 80 connected to network 14. Videophone 80 is connected to a standard telephone 81 and to a laptop type computer 82 by audio, video, and data/control links. Computer 82 includes display 84, modem 86, optional network interface 88, optional RS-232 interface 90, computer memory 92, IRDA interface 94, floppy disk drive 96, hard disk drive 98 (storing an OS such as WINDOWS 95/98), laptop mouse 100, laptop keyboard 102, parallel port 104, battery 106, date/time clock 108, steth processor 110, retransmit higher resolution command control 112. Connected to computer 82 is a camera 114 (which can also be connected to video phone 80), sound reproducer (speaker, headphones) 116, external I/O devices 118 (external mouse, external keyboard, external RS-232 link, external printer), and external power 120. Units 80 and 82 can be housed in the same case or be housed in separate but connected cases.

The digital image(s) and digital stethoscope data are received in the data channel of second videophone 80. The digital stethoscope data is sent to steth processor 110 of computer 82 (e.g., video phone data channel is sent to a IIC serial output port, the IIC serial data is converted to a RS-232 serial stream of data, the RS-232 serial stream of data is sent to a RS-232 port of computer 82, and stored in memory 92, the memory is read into steth processor 110. Steth processor 110 converts the digital stethoscope sound data to analog data by a digital-to-analog converter. The analog signal is amplified, sent to a power amplifier and then to sound reproducer 116 for the health care provider to hear the stethoscope sounds. The digital images are converted and displayed on display 84.

If a user desires a higher quality audio sound, the user will actuate control 112 to send a command to the data channel of second videophone 80. The first videophone 18 will receive the command over the data channel from videophone 80, adjust the loss ratio of compressor 42 (FIG. 3), recompress the stethoscope sound data in buffer memory 38 to a higher quality sound data and retransmit the stethoscope sound data from videophone 18 to videophone 80 over network 14. The user at station 16 hears the higher quality stethoscope sounds by sound reproducer 116.

The invention has been described in detail with particular reference to certain preferred embodiments thereof, but it will be understood that variations and modifications can be effected within the spirit and scope of the invention.

PARTS LIST

| PARTS LIST |
| --- |
| 10 home health care system |
| 12 patient station |
| 14 public telecommunication network |
| 16 health care provider's station |
| 18 first videophone |
| 20 processor |
| 22 stethoscope |
| 24 camera |
| 26 standard telephone |
| 28 video display |
| 30 stethoscope processing circuit |
| 32 transducer |

-continued

PARTS LIST 34 volume and filter section
36 analog to digital converter
38 recirculating buffer memory
40 direct memory access controller (DMA)
42 tunable loss audio compressor
44 first-in-first-out (FIFO) memory
46 input/output (I/O)
48 bus
50 memory
52 hard drive
54 CPU
56 keyboard
58 mouse
60 external power source
62 blood pressure device
64 patient thermometer
66 weight scale
68 finger sensor
70 peak flow meter
72 room temperature device
74 audio output (speaker)
76 local stethoscope output
80 second videophone
81 standard telephone
82 laptop type computer
84 display
86 modem
88 optional network interface
90 optional RS-232 interface 90
92 computer memory
94 IRDA interface
96 floppy disk drive
98 hard disk drive
100 laptop mouse
102 laptop keyboard
104 parallel port
106 battery
108 date/time clock
110 steth processor
112 retransmit higher resolution command control
114 camera
116 sound reproducer
118 external I/O devices
120 external power

What is claimed is:

1. A health care system comprising:

a patient station including a first videophone, an electronic imaging assembly and a stethoscope assembly, coupled to said first videophone, for respectively producing digital image and physiological sound signals of a patient, wherein said first videophone simultaneously transmits said digital signals over a public telecommunications network;

a health care provider's station including a second videophone, a video display and a sound reproducer, wherein said second videophone receives said digital signals from said first videophone over said public telecommunications network, displays said images of said patient on said display, and reproduces said physiological sounds of said patient by said sound reproducer;

wherein said stethoscope assembly includes a transducer for transducing physiological sounds of a patient into analog signals, a converter for converting said analog signals into raw digital physiological sound data, a recirculating buffer memory for storing said raw digital physiological sound data, a digital data compressor for compressing said raw digital physiological sound data by a compression ratio that is selectable over a range of compression ratios, and a memory for storing said compressed physiological sound data, wherein said first videophone transmits said compressed data over said network to said second videophone; and wherein said health care provider's station includes a control for commanding said compressor at said patient's station to compress said raw digital physiological sound signals at a lower compression ratio into newly compressed digital sound data to produce higher quality sound, and to retransmit said newly compressed data over said network for reproduction at said health care provider's station.

* * * * *